US 6,804,325 B1

(12) United States Patent
Smith (10) Patent No.: US 6,804,325 B1
(45) Date of Patent: Oct. 12, 2004

(54) METHOD FOR POSITION EMISSION MAMMOGRAPHY IMAGE RECONSTRUCTION

(75) Inventor: Mark Frederick Smith, Yorktown, VA (US)

(73) Assignee: Southeastern Universities Research Assn., Newport News, VA (US)

( * ) Notice: Subject to any disclaimer, the term of this patent is extended or adjusted under 35 U.S.C. 154(b) by 283 days.

(21) Appl. No.: 10/280,699

(22) Filed: Oct. 25, 2002

(51) Int. Cl.[7] .............................. A61B 6/23; G61T 1/166

(52) U.S. Cl. .................................... 378/37; 250/363.02

(58) Field of Search ................................ 378/4, 37, 62, 378/901; 250/363.02, 363.04

(56) References Cited

U.S. PATENT DOCUMENTS 5,793,045 A * 8/1998 DiFilippo et al. ...... 250/363.03
5,969,358 A * 10/1999 DiFilippo et al. ...... 250/363.03

OTHER PUBLICATIONS

Analysis of factors affecting position emission mammography (PEM) Image Formation Smith, Majsuski, Wrisenbtager, Kieper, Raylman & Turkington.

* cited by examiner

Primary Examiner—David V. Bruce (57) ABSTRACT

An image reconstruction method comprising accepting coincidence datat from either a data file or in real time from a pair of detector heads, culling event data that is outside a desired energy range, optionally saving the desired data for each detector position or for each pair of detector pixels on the two detector heads, and then reconstructing the image either by backprojection image reconstruction or by iterative image reconstruction. In the backprojection image reconstruction mode, rays are traced between centers of lines of response (LOR's), counts are then either allocated by nearest pixel interpolation or allocated by an overlap method and then corrected for geometric effects and attenuation and the data file updated. If the iterative image reconstruction option is selected, one implementation is to compute a grid Siddon retracing, and to perform maximum likelihood expectation maiximization (MLEM) computed by either: a) tracing parallel rays between subpixels on opposite detector heads; or b) tracing rays between randomized endpoint locations on opposite detector heads.

4 Claims, 13 Drawing Sheets

Conventional backprojection algorithm, 1.65 mm pixels

Figure 7

New backprojection formula, 1.65 mm pixels, overlap count allocation

Iterative MLEM algorithm, 1.65 mm pixels, 1 ray/TOR

Transaxial slice     vertical profile

Coronal slice     vertical profile

Figure 11

Iterative MLEM algorithm, 1.65 mm pixels, 16 rays/TOR

Figure 12

Uniformity map

Slice 1  Slice 10  Slice 20

Slice 30

METHOD FOR POSITION EMISSION MAMMOGRAPHY IMAGE RECONSTRUCTION

The United States of America may have certain rights to this invention under Management and Operating Contract DE-AC05-84ER 40150 from the United States Department of Energy.

FIELD OF THE INVENTION

The present invention relates to positron emission mammography, and more particularly to methods and apparatus for positron emission mammography image reconstruction.

BACKGROUND OF THE INVENTION

Functional imaging of the breast with F-18 fluorodeoxyglucose (FDG) has the capability to differentiate metabolically active tumors and is being investigated for the detection, staging and treatment of breast cancer. Clinical breast imaging with FDG has been performed with conventional positron emission tomography (PET) scanners as well as with dedicated positron emission mammography (PEM) devices. There have been many proposed designs for PEM detectors, which have the potential for improved sensitivity and spatial resolution compared with conventional PET scanners. Initial clinical results have been reported only for the dual planar detector configuration, however.

For a PEM device with the breast positioned between two static planar detectors, image reconstruction is usually performed by backprojection along the lines of response (LORs) to the desired image planes [18]. A lesion is focused when an image is formed in the plane in which it is located, while out-of-plane activity appears blurred. In this contribution three major factors affecting PEM image formation by the backprojection method are investigated: image uniformity (flood) corrections, image sampling (pixel size) and count allocation methods. In addition, enhanced PEM image reconstruction by iterative matrix methods is described.

Image uniformity is dependent on spatially dependent geometric and detector sensitivity factors.

In conventional PEM the source region or tissue with positron-emitting activity, for example F-18 fluorodeoxyglucose (FDG), is placed between two detectors operated in coincidence mode. The detectors are capable of detecting the two 511 keV photons resulting from positron annihilation following radioactive decay and positron emission. The detector heads are parallel to each other. Images of the source distribution can be formed by backprojecting events (counts) along the line of response (LOR) connecting the centers of the detection pixels in the two detector heads. In planes parallel to the detector heads, counts are allocated to the pixel through which the LOR passes. This method of count allocation is also sometimes termed the nearest neighbor or closest pixel approximation. The contribution of an event may be weighted using a detection probability (See C. J. Thompson, K Murthy, Y. Picard, I. N. Weinberg, and R. Mako, "Positron Emission Mammography (PEM): A Promising Technique for Detecting Breast Cancer," *IEEE Transactions on Nuclear Science*, vol. 42, pp. 1012–1017, 1995).

This method of image reconstruction by backprojection is also known as laminography. In some implementations images are reconstructed using only those events whose raypaths are within a certain maximum angle from normal incidence with the detectors and without a uniformity correction (See R. R. Raylman, S. Majewski, R. Wojcik, A. G. Weisenberger, B. Kross, V. Popov, and H. A. Bishop, "The Potential Role of Positron Emission Mammography for Detection of Breast Cancer. A Phantom Study," *Medical Physics*, vol. 27, pp. 1943–1954, 2000). These images exhibit non-uniformities in part because the number of lines of response through a pixel in the reconstructed image varies as a function of the pixel's spatial position. Uniformity corrections are sometimes applied using measured data from activity in a uniform box phantom taken at a single position between the detectors.

The spatial dependence of positron camera sensitivity has been previously noted and displayed in FIG. 12 of Muehllehner et al. (See G. Muehllehner, M. P. Buchin, and J. H. Dudek, "Performance Parameters of a Positron Imaging Camera," *IEEE Transactions on Nuclear Science*, vol. NS-23, pp. 528–537, 1976). The geometric efficiency of a circular planar positron camera has been studied by Weathersby et al. (See P. K. Weathersby, S. S. Survanshi, and P. Meyer, "Spatial Sensitivity of a Planar Positron Camera," *Nuclear Instruments and Methods in Physics Research*, vol. 220, pp. 571–574, 1984). PEM detectors also have been developed by Irving Weinberg [1984] (See I. N. Weinberg, S. Majewski, A. G. Weisenberger, A. Markowitz, L. Aloj, L. Majewski, D. Danforth, J. Mulshine, K Cowan, J. Zujewski, C. Chow, E. Jones, V. Chang, W. Berg, and J. Frank, "Preliminary Results for Positron Emission Mammography: Real-time Functional Breast Imaging in a Conventional Mammographic Gantry," *European Journal of Nuclear Medicine*, vol. 23, pp. 804–806, 1996), and in our laboratory (See R. R. Raylman, S. Majewski, R. Wojcik, A. G. Weisenberger, B. Kross, V. Popov, and H. A. Bishop, "The Potential Role of Positron Emission Mammography for Detection of Breast Cancer. A Phantom Study," *Medical Physics*, vol. 27, pp. 1943–1954, 2000).

Nearest neighbor count allocation in backprojection reconstruction may result in banding or pixelization artifacts in the reconstructed image if the pixel size in the reconstructed image is smaller than the detector pixel size. Such artifacts have been seen in images reconstructed using PEM detectors built at Jefferson Lab. Banding and pixelization artifacts are visible in PEM image reconstructions in FIG. 5 of K. Murthy, M. Aznar, C. J. Thompson, A. Loutfi, R. Lisbona, and J. H. Gagnon, "Results of preliminary clinical trials of the positron emission mammography system PEM-I: a dedicated breast imaging system producing glucose metabolic images using FDG," *Journal of Nuclear Medicine*, vol. 41, pp. 1851–1858, 2000.

Freifelder and Karp in R. Freifelder and J. S. Karp, "Dedicated PET Scanners for Breast Imaging," *Physics in Medicine and Biology*, vol. 42, pp. 2463–2480,1997 implemented iterative image reconstruction for numerical simulations of dual detector PEM, but only after rebinning the coincidence data using the single slice rebinning algorithm. Iterative reconstructions were performed for each slice separately, thus image reconstruction of the entire three-dimensional source region was not performed at the same time, which is desirable in order to obtain the most likely (in the statistical sense) estimate of source activity in the 3-D region between the detectors.

While all of the foregoing analysis and image data manipulation techniques provided useful and highly valuable information, certain image artifacts that resulted when the image reconstruction pixel size was smaller than the detector pixel tended to distort the image. In the case of back projection reconstruction, because of the "slice reconstruction" approach used, the lesion contrast tended to be somewhat reduced.

OBJECT OF THE INVENTION

It is therefore an object of the present invention to provide computer programs and formulae that enhance the quality of the PEM acquired image for more accurate detection and localization of a potential lesion

SUMMARY OF THE INVENTION

The method of the present invention uses list mode event data acquired from a dual head positron emission mammography detector or from numerical simulations of event data from such a detector. A computer program reads in the event data, performs the image reconstructions and writes out a binary file with the reconstructed image. This computer program can perform both backprojection image reconstruction and iterative image reconstruction. A copy of the source code to this program is attached hereto as Appendix A.

The image reconstruction method of the resent invention comprises accepting coincidence data from either a data file or in real time from a pair of detector hgeads, culling event data that is outside of a desired energy range, saving the disried data for each detector position or for each pair of detector pixels on the two detector heads, and the reconstructing the image either by backprojection image reconstruction or by iterative image reconstruction. In the backprojection image reconstruction mode, rays are traced between centers of lines of response (LOR's), a probability factor computed and augmented with an attenuation factor, if desired, counts are then either allocated by nearest pixel interpolation or allocated by an overlap method and then corrected for geometric effects and attenuation and the image file updated. If the iterative image reconstruction option is selected then for this particular implementation a grid is computed for Siddon retracing, and maximum likelihood expectation maximization (MLEM) images are computed by either: a) tracing parallel rays between subpixels on opposite detector heads; or b) tracing rays between randomized endpoint locations on opposite detector heads. Various augmentive attenuation and normalization factors and probabilities are optionally applied and partial sums for the MLEM algorithm are accumulated.

DETAILED DESCRIPTION

According to the present invention, for list-mode event files, the number of coincidence events between any two pairs of pixels in opposite detectors meeting user-defined energy cutoffs and acceptance angle cutoffs is computed. Then, a new method of count allocation is employed that involves the random selection of the coordinates of the endpoints of rays in the two detectors or the selection at endpoints according to the centers of subpixels of the detector pixels. Additionally, a tube of response method of sampling the data is used and coincidences within the tube of response are overlaid, i.e. proportioned among the pixels impacted according to the number of counts received by each detecting pixel. Alternatively, the coincidence events are allocated to image pixels that are intersected by the raypaths.

Figure 1:
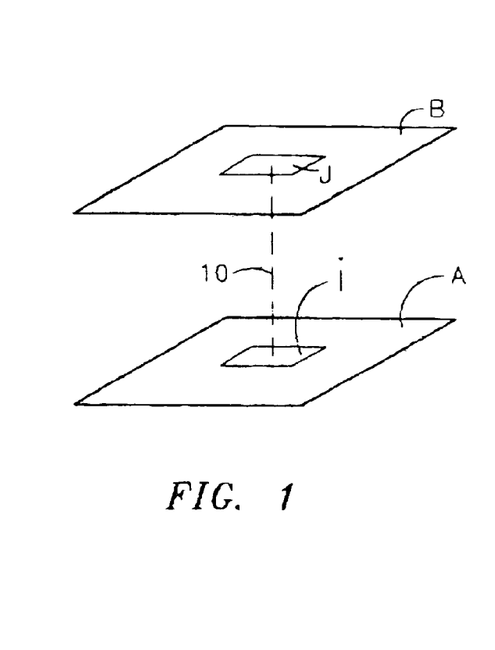
FIG. 1 depicts the conventional method of image data collection for a coincidence event.
Figure 2:
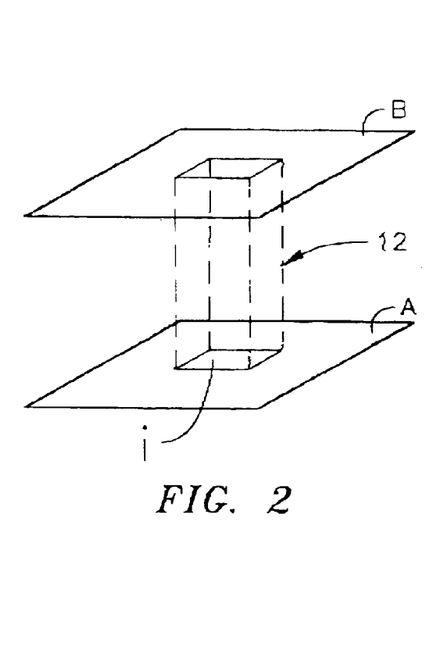
FIG. 2 depicts the tube of response between pixel heads on two detector heads for a coincidence event.
Figure 3:
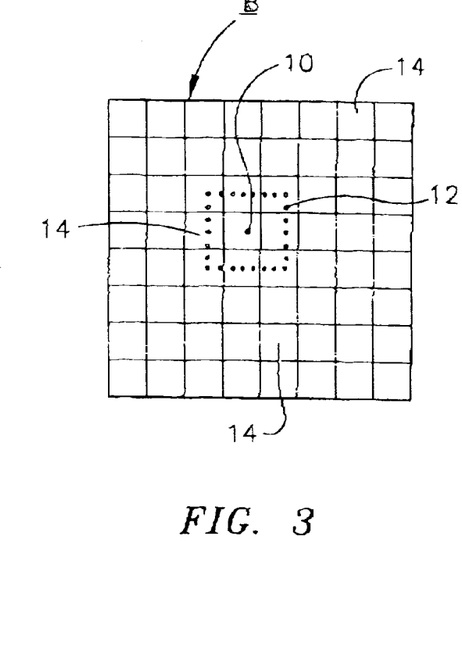
FIG. 3 depicts an 8×8 pixel image plane. The dashed square shows the intersection of a tube of response with this image plane and the dot represents the intersection of the line of response for the same coincidence event with this image plane.

Referring now to FIGS. 1 and 2, consider a coincidence event that is detected in pixel i of detector A and pixel j of detector B. In conventional backprojection image reconstruction a line of response (LOR) is drawn between the pixel centers, 10 in FIG. 1, and the counts are allocated to the pixel in the image plane that this LOR intersects. However, the positron annihilation could have originated anywhere within the tube of response (TOR), 12 in FIG. 2, connecting the two detection pixels. For square detector pixels the intersection of tube 12 with any image plane parallel to the detector heads 14 is a square as shown in FIG. 3. In the image reconstruction method of the present invention, a fractional number of counts is allocated to an image pixel in proportion to the area of the backprojected square that overlaps the image pixel as shown in FIG. 3. Stated somewhat differently, a line of response (LOR) 10 connects the centers of the two detection pixels for a coincidence event, FIG. 1. Dashed lines outline the borders of the tube of response (TOR) FIG. 2 between pixels on two detector heads A and B for a coincidence event.

A different way of implementing this count allocation method is used for real-time or post processing image reconstruction implemented in accordance with the present invention. For each detected coincidence event, the endpoints of the line of response 10 are randomly chosen within the detection pixels by the reconstruction software. The event is then allocated to the pixel in the image plane that the LOR intersects. The effect of this uniform, random sampling process is to have LORs approximately uniformly sample the tube of response 12 connecting the detector pixels, minimizing or avoiding discretization artifacts in the reconstructed images.

According to the present invention, a backprojection image uniformity map is computed by forming images as described above, except that the contribution from any tube of response 12 is unity or a computed sensitivity factor rather than a number that is proportional to the number of detected coincidence events for a detector pair. A uniformity correction map is computed by taking the pixel-by-pixel multiplicative inverse of the uniformity map. The uniformity correction map is used to multiply the uncorrected image produced as described above. Uniformity maps and uniformity correction maps are then computed for each image plane.

Iterative image reconstruction is performed using the iterative maximum likelihood expectation maximization (MLEM) algorithm (See K. Lange and R. Carson, "EM reconstruction algorithms for emission and transmission tomography," *Journal of Computer Assisted Tomography*, vol. 8, pp. 306–316, 1984) with a system matrix designed specifically for PEM. This algorithm solves the matrix equation d=A s for the three-dimensional source activity distributions from the observed coincidence data d. The elements of the data vector d are the observed number of coincidence events between each coincidence pixel pair; all pairs are included, not just pairs for which the LORs lie in a single plane. For example, if detector head A has m pixels and head B has n pixels, the data vector d will have m.n elements. The elements of the system matrix A are computed using the Siddon raytracing method (See R. L. Siddon, "Fast Calculation of the Exact Radiological Path for a Three-dimensional CT Array," *Medical Physics*, vol. 12, pp. 252–255, 1985) and may include a sensitivity correction using a formula similar to that described in R. H. Huesman, G. J. Klein, W. W. Moses, J. Qi, B. W. Reutter, and P. R. G. Virador, "List-mode Maximum-likelihood Reconstruction Applied to Positron Emission Mammography (PEM) with Irregular Sampling," *IEEE Transactions on Medical Imaging*, vol. 19, pp. 532–537, 2000. Image reconstruction is a case of limited angle tomography for stationary detector heads. Angular sampling is incomplete and thus there will be blurring between the detectors, if the acquisition is with the detectors in a static position. Iterative image reconstruction also can be performed where the PEM detectors rotate around the object to be imaged.

Figure 4:
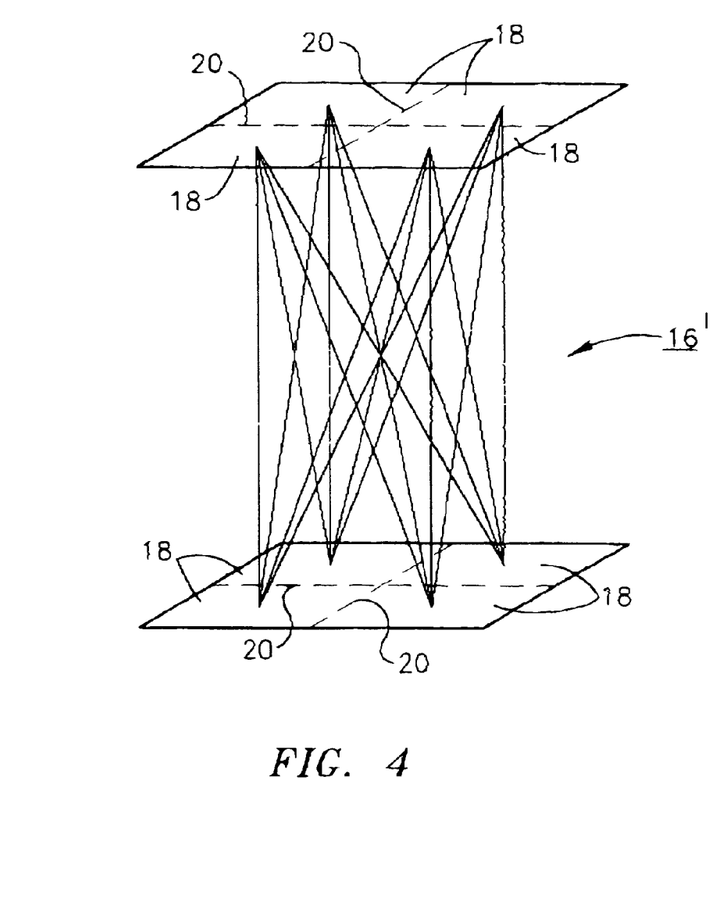
FIG. 4 depicts a first detector pixel subsampling and raytracing scheme.
Figure 5:
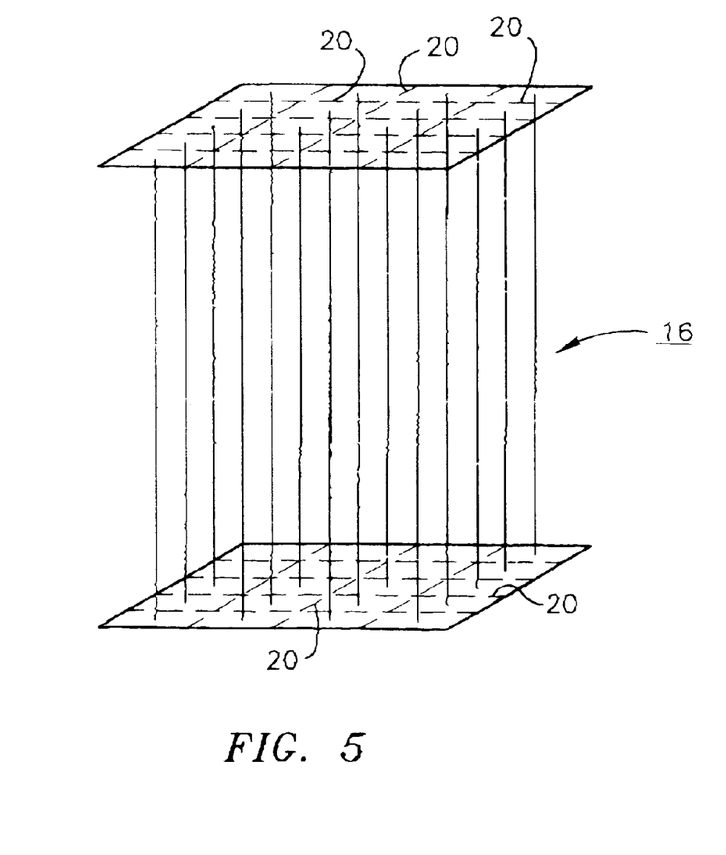
FIG. 5 depicts a second detector pixel subsampling and raytracing scheme.

There are program options to subsample the detector pixels and to trace multiple rays between detector pixel pairs in order to sample the tubes of response more finely FIGS. 4 and 5. These options permit improved modeling of the physics of data acquisition. FIGS. 4 and 5 show examples of two different detector pixel subsampling and raytracing: schemes. Rays 16 are traced within the TOR connecting the detection pixels 18. Dashed lines 20 denote subpixel boundaries. In FIG. 4 rays 16 are traced between all subpixels 18 during iterative image reconstruction. In FIG. 5 only rays16 parallel to the LOR connecting the pixel centers are traced between detector subpixels 18 during iterative image reconstruction.

EXAMPLES

The following examples will serve to better illustrate the successful practice of the present invention.

Conventional vs. Inventive PEM Breast Phantom Reconstruction

All image data was acquired using a pair of parallel plate PEM detectors as shown in FIGS. 1 and 2 after injection of the phantom with F-18. Data acquisition parameters: 4 cm thick compressed breast phantom with 5, 9,12,16 mm diameter lesions Lesion:background F-18 concentration ratio =8.5:1 Detector separation 20 cm GSO detector in coincidence mode; pixel pitch 3.3 mm, pixel width 3.0 mm Active detector pixels: 29×29 array Reconstruction parameters: Energy window 400–700 keV; 115724 coincidence events All angles accepted during image reconstruction (no maximum) 30×30 pixel image array, 30 slices, 3.30 mm pixels, slice spacing 3.30 mm 60×60 pixel image array, 60 slices, 1.65 mm pixels, slice spacing 1.65 mm

Example 1

Figure 6:
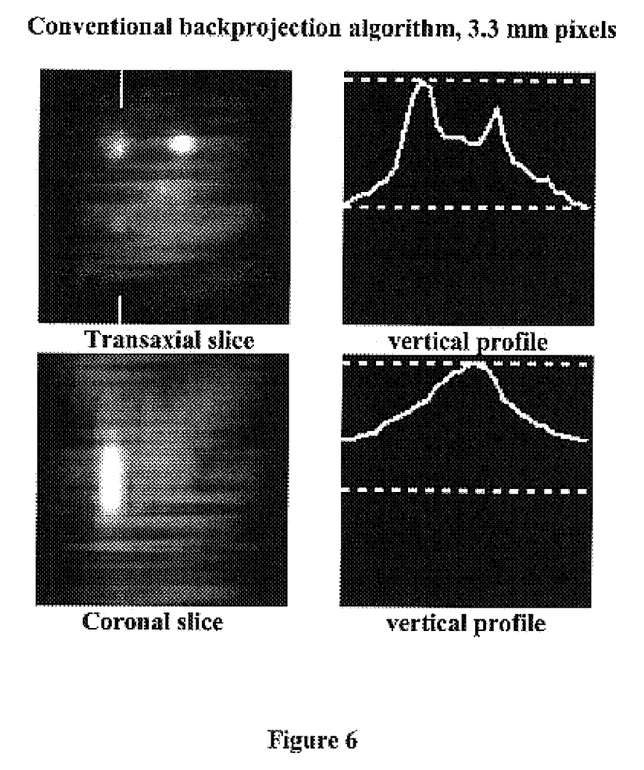
FIGS. 6–16 show results of various image reconstructions and their analysis.
Figure 7:
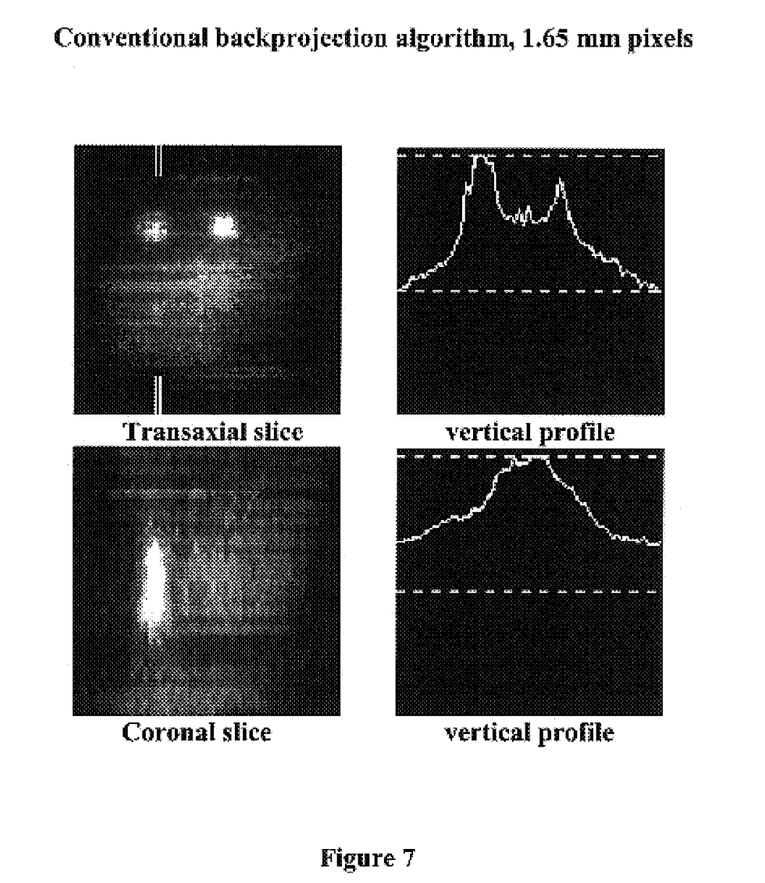
Figure 8:
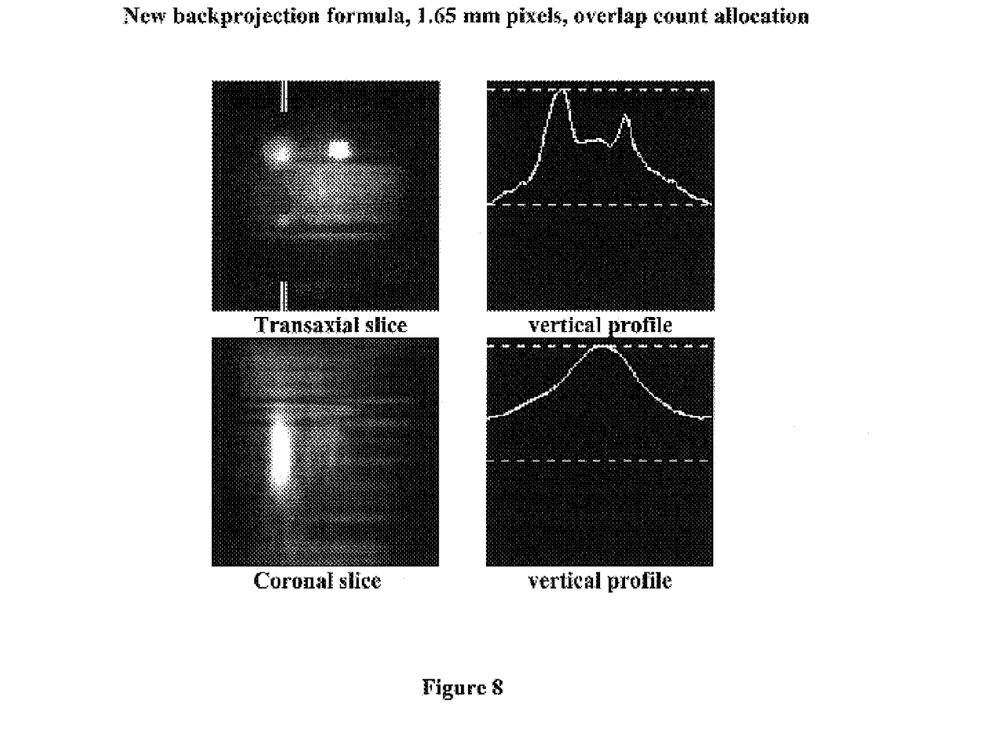
Figure 9:
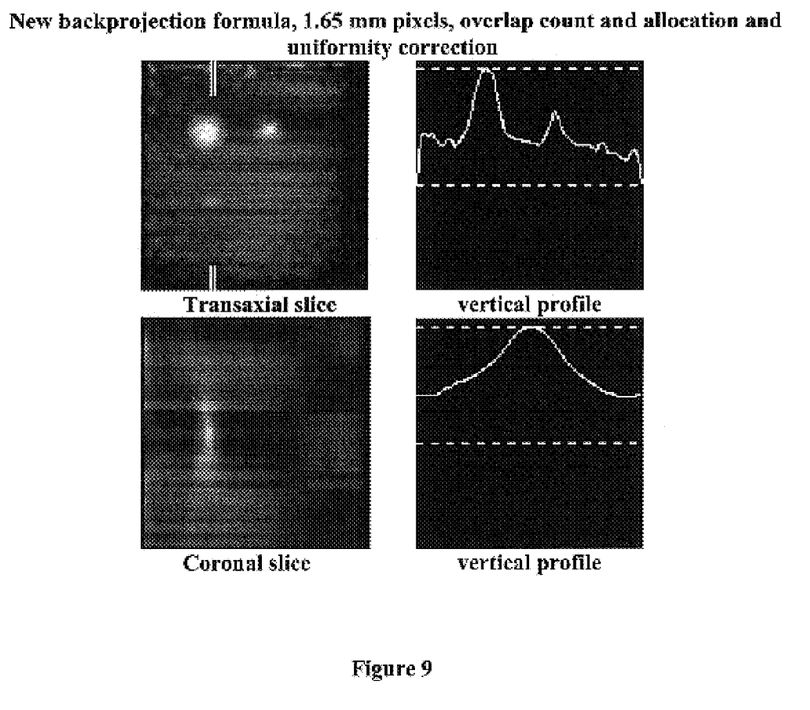

Reconstructions using the foregoing parameters and comparing the conventional backprojection formulae FIGS. 6 and 7 and those of the present invention are compared in FIGS. 8 and 9. In studying the results depicted in FIGS. 6 and 7, note should be taken of the banding and artifacts and that the contrast of small lesions is improved with smaller reconstruction pixels. In FIG. 8, the elimination of banding and pixelization artifacts should be noted. In FIG. 9, note should be taken of the improved uniformity over the field of view with any remaining image non-uniformities being due to intrinsic detector factors or to source distribution effects.

Example 2

Figure 10:
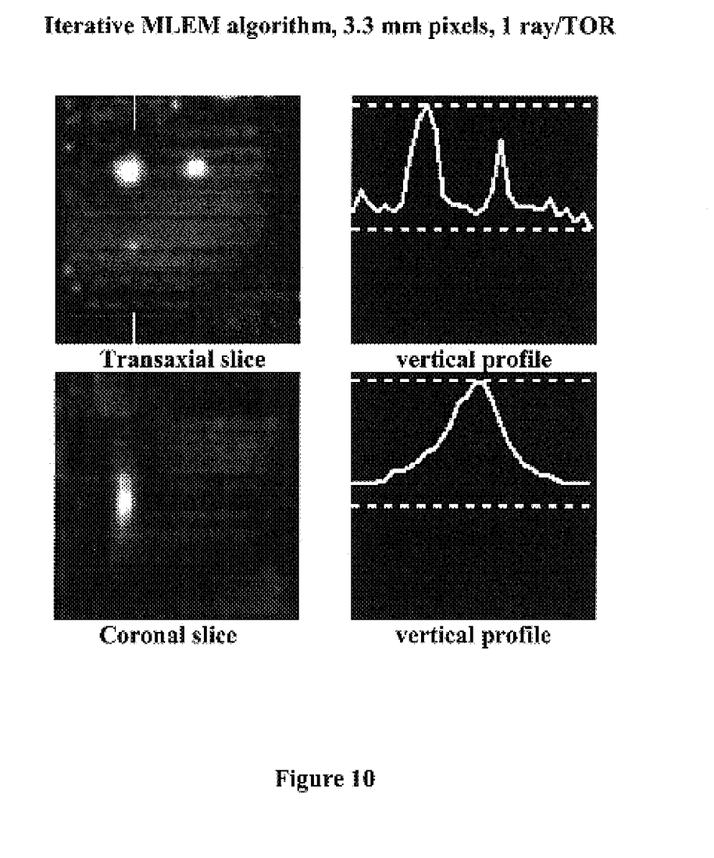

Iterative MLEM formulae, 3.3 mm pixels, 1 ray/TOR results are depicted in FIG. 10. In these examples, lesion contrast is improved compared with backprojection reconstruction, at the expense of some additional image noise. A discontinuity is visible at the midline of the coronal slice.

Example 3

Figure 11:
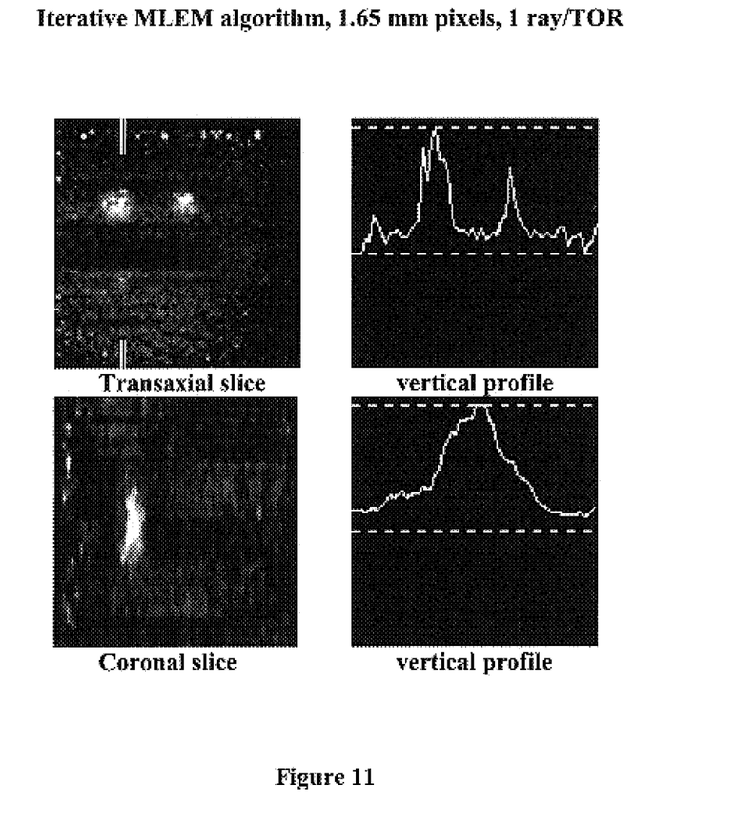

Iterative MLEM formulae, 1.65 mm pixels, 1 ray/TOR results are depicted in FIG. 11. The high frequency content of the images is slightly improved by the use of smaller pixels, at the expense of lower signal-to-noise ratio. A discontinuity is visible at the midline of the coronal slice.

Example 4

Figure 12:
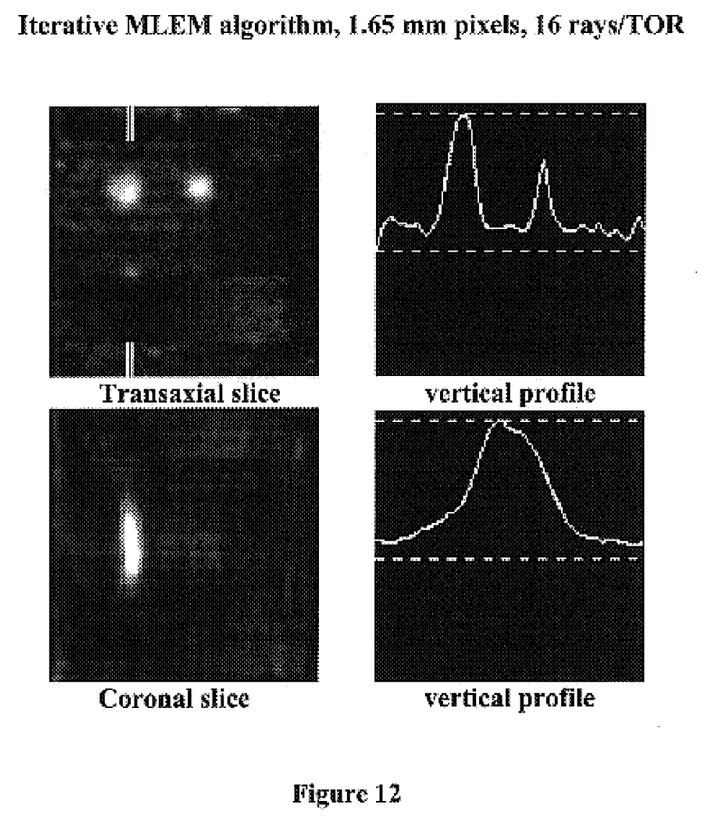

Iterative MLEM formulae, 1.65 mm pixels, 16 rays/TOR are depicted in FIG. 12. The signal-to-noise ratio is increased because the physics of data acquisition is better modeled by tracing 16 rays, rather than 1 ray, through the tube of response for each detector pixel pair during image reconstruction.

Example 5

Figure 13:
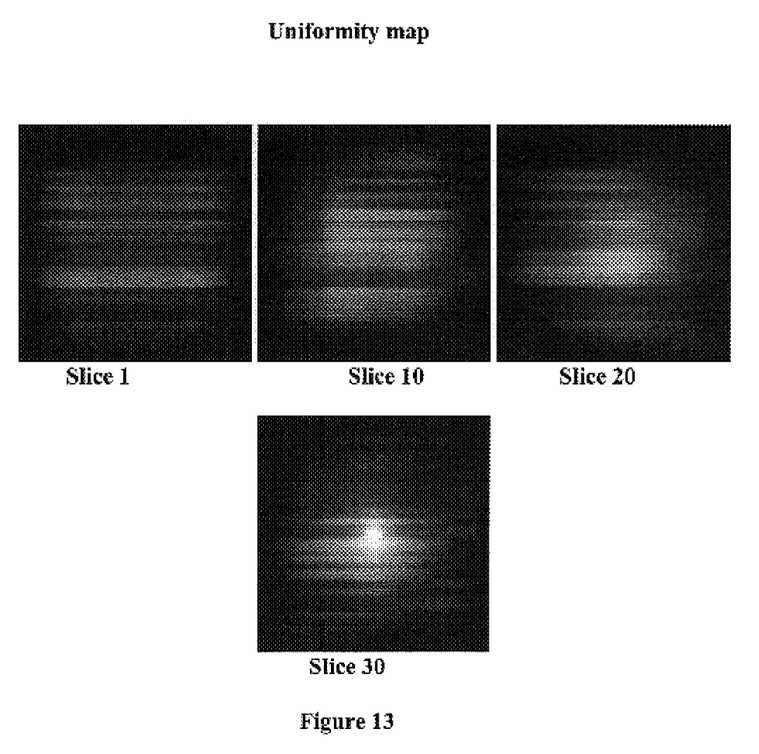
Figure 14:
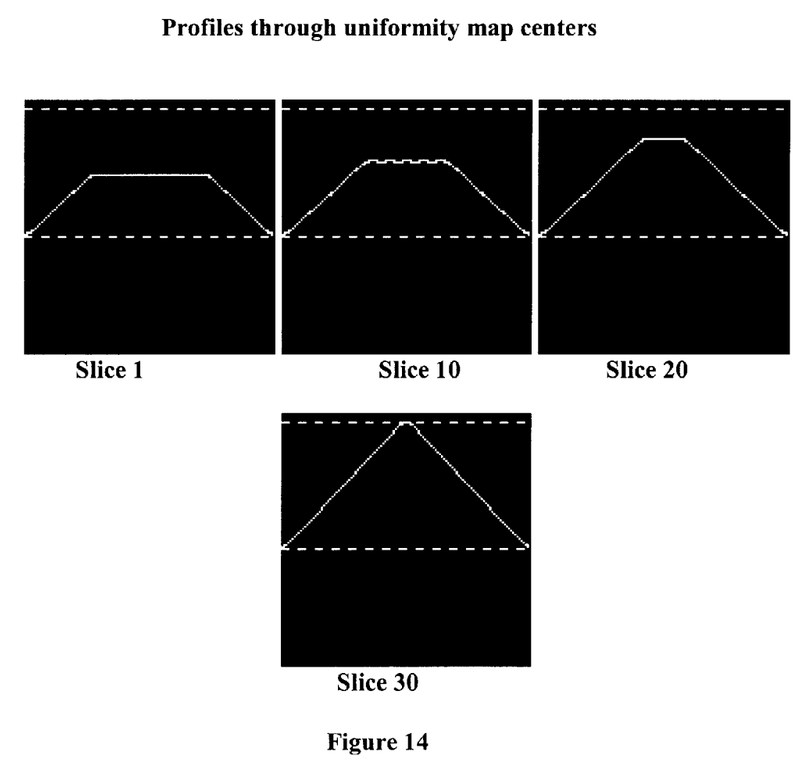
Figure 15:
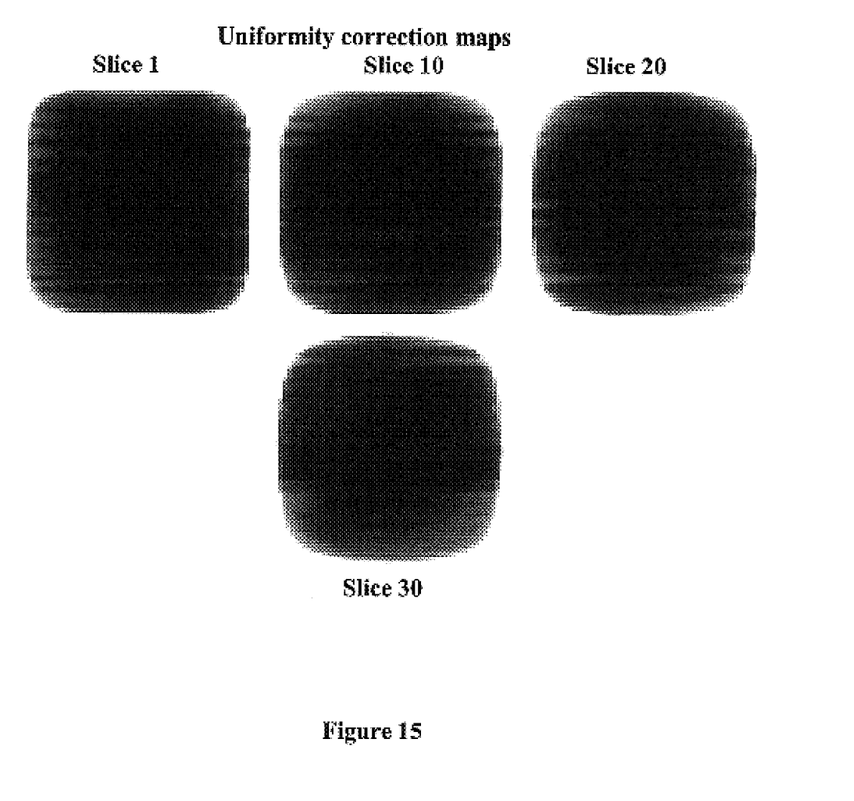
Figure 16:
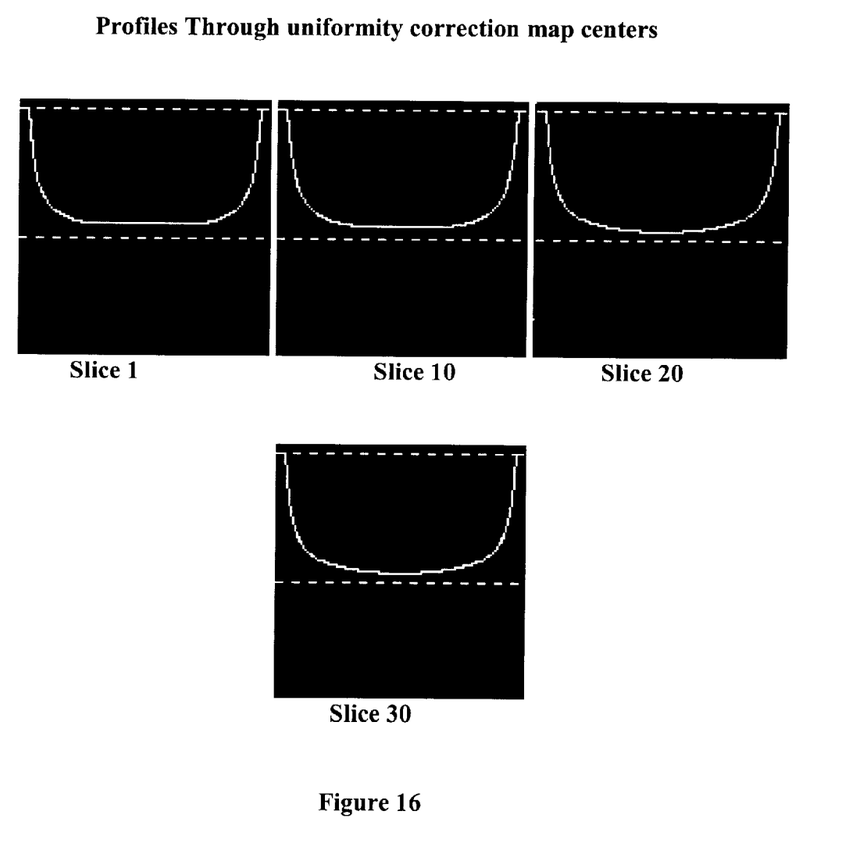

Backprojection reconstruction uniformity maps and profiles of the computed number of LOR tubes passing through a reconstructed pixel are displayed in FIGS. 13 and 14. Uniformity correction maps and profiles for the results presented in FIG. 13 and 14 are shown in FIGS. 15 and 16. Correction maps are the inverse of the uniformity maps of FIGS. 13 and 14 and are applied as part of the new backprojection formula. The maximum relative correlation factor is limited to 20 in these plots; profiles are through the center pixel.

There has thus been described and demonstrated an overlap method of event count allocation. The intersection of the tube of response (corresponding to a line of response) between two square pixels on opposed detector heads is a square in image planes that are parallel to these detector heads. Counts are allocated to image pixels in proportion to the area of this square that they overlap.

The method for achieving approximately uniform sampling of the tube of response for real-time or post-processing image formation, using a randomization method for choosing the coordinates of the ends of the line of response within the detector pixels rather then always using the pixel centers is a way of implementing the overlap count allocation method.

The image uniformity correction technique does not rely on integration formulas and thus can handle non-regular detector geometries or the case of bad detector pixels, for which detector pixel pairs must be excluded from image reconstruction.

The overlap method of count allocation is general enough that it can be used to reconstruct images by backprojection along arbitrary curvilinear surfaces with uniformity correction.

The overlap method of count allocation will work for any two detectors in coincidence mode, not just for PEM detectors or for breast imaging. The detectors can be in any relative orientation, not necessarily parallel to each other.

One program can perform backprojection reconstruction using both the nearest pixel and overlap methods of count allocation.

This method has been implemented for two static detector heads, but it can be used to handle data acquired for two detector positions or multiple detector positions for tomographic imaging with complete angular sampling over 360 degrees. In other words, a method has been described for the generation of fully three-dimensional image reconstruction in PEM, with or without complete angular sampling, by using iterative image reconstruction methods.

The method described can be used for iterative image reconstruction for limited angle tomography, for example, iterative image reconstruction for limited angle tomography in nuclear medicine or iterative image reconstruction for limited angle tomography in PEM imaging.

Among the other novel features of the method of the present invention are: use of the tube of response (TOR) method for determining system matrix elements for iterative image reconstruction between detection pixel pairs in coincidence detectors; use of the TOR method for projection and backprojection with any image reconstruction method in medical imaging, nuclear medicine, positron emission imaging or positron emission tomography; the use of the TOR method with any type of coincidence detectors in positron imaging, e.g. PEM detectors, ring PET scanners, dual head gamma cameras operated in coincidence mode; and the use of the TOR method for positron emission tomography (PET) image reconstruction.

The method of the present invention provides multiple ways of choosing raypaths for iterative reconstruction to achieve better sampling of tubes of response associated with detection pixel pairs in coincidence detectors, rather than using just a single ray connecting the pixel centers. The subpixelization method for ray tracing in iterative reconstruction, with rays traced between all subpixel pairs is also made possible. Alternatively, subpixelization with only the use of rays parallel to the ray connecting the pixel centers in iterative reconstruction can be performed.

According to the method of the present invention, the image reconstruction pixels for PEM reconstruction can be of arbitrary sizes, not necessarily the same as the detector pixel size or the detector pixel size divided by an integer. The location of the image planes between detectors can also be arbitrarily set.

Computers and computer equipment useful in the execution of the code described in this application and attached hereto as Appendix A are well known to those skilled in the art of image reconstruction and need not be described further in connection herewith.

Detailed descriptions of the various algorithms applied in the attahed computer code for the calculation and manipulation of image data for the production of both backprojection and iterative image reconstruction are presented in greater detail in the following paper at the IEEE Medical Imaging Conference meeting of Nov. 4–10, 2001, Analysis of Factors Affecting Positron Emission Mammography (PEM) Image Formation", Mark F. Smith, Stan Majewski, Andrew G. Weisnberger, Douglas Kieper, Raymond R. Raylman and Timothy G. Turkington accepted for publication in IEEE Trans. Nucl. Sci. the contents of which are incorporated herein by reference in their entirety as if the paper were reproduced herein in its entirety.

As the invention has been described, it will be apparent to those skilled in the art that the same may be varied in many ways without departing from the spirit and scope of the invention. Any and all such modifications are intended to be within the scope of the appended claims.

What is claimed is:

1. An image reconstruction method comprising:
    A) accepting coincidence data from either a data file or in real time from a pair of detector heads;
    B) culling event data that is outside a desired energy range; and
    C) reconstructing a three dimensional image by either;
        i) a backprojection image reconstruction method comprising:
            a) tracing rays between centers of lines of response;
            b) allocating counts by nearest pixel interpolation or by an overlap method; or
        ii) an iterative image reconstruction method.

2. The method of claim 1 further including the steps of correcting for geometric and attenuation effects after backprojection image or iterative image reconstruction.

3. The method of claim 1 wherein said iterative image reconstruction method is accomplished by:
    a) computing a grid for Siddon retracing; and
    b) computing maximum likelihood expectation maximization (MLEM) by either;
        1) tracing parallel rays between subpixels on opposite detector heads; or
        2) tracing rays between randomized endpoint locations within detector pixels on opposite detector heads.

4. The method of claim 1 further including saving the desired data for each detector position or for each pair of detector pixels on the two detector heads after step B and before step C.

* * * * *

UNITED STATES PATENT AND TRADEMARK OFFICE
CERTIFICATE OF CORRECTION

PATENT NO. : 6,804,325 B1
DATED : October 12, 2004
INVENTOR(S) : Mark Frederick Smith It is certified that error appears in the above-identified patent and that said Letters Patent is hereby corrected as shown below:

Title page, Item [54] and Column 1, line 1,
Title, change "POSITION" to -- POSITRON --.

Title page,
Item [56], References Cited, OTHER PUBLICATIONS, change "position" to
-- positron -- and change "Majsuski, Wrisenbtager" to -- Majewski, Weisenberger --.
Item [57], ABSTRACT,
Line 2, change "datat" to -- data --;
Line 14, insert -- for -- between "grid" and "Siddon"; and
Line 16, change "maiximization" to -- maximization --.

Column 3,
Line 19, change "resent" to -- present --;
Line 21, change "hgeads" to -- heads --;
Line 23, change "disried" to -- desired --;
Line 24, change "the" (second occurrence) to -- then --;

Column 7,
Line 46, change "attah" to -- attach --;

Column 8,
Line 6, change "Weisnberger" to -- Weisenberger --.

Signed and Sealed this

Twenty-fifth Day of January, 2005

JON W. DUDAS
*Director of the United States Patent and Trademark Office*